(12) United States Patent
Sterrett et al.

(10) Patent No.: US 10,548,671 B2
(45) Date of Patent: Feb. 4, 2020

(54) MEDICAL DEVICE WITH A PACKAGED ELECTRONIC SUBASSEMBLY AND METHOD FOR FABRICATING THE SAME

(71) Applicant: St. Jude Medical International Holding S.à r.l., Luxembourg (LU)

(72) Inventors: Terry L. Sterrett, Huntington Beach, CA (US); Patrick P. Senarith, Tustin, CA (US)

(73) Assignee: St. Jude Medical International Holding S.á r.l., Luxembourg (LU)

( * ) Notice: Subject to any disclaimer, the term of this patent is extended or adjusted under 35 U.S.C. 154(b) by 208 days.

(21) Appl. No.: 15/114,011

(22) PCT Filed: Jan. 27, 2015

(86) PCT No.: PCT/US2015/013010
§ 371 (c)(1),
(2) Date: Jul. 25, 2016

(87) PCT Pub. No.: WO2015/116562
PCT Pub. Date: Aug. 6, 2015

(65) Prior Publication Data
US 2016/0346045 A1    Dec. 1, 2016

Related U.S. Application Data

(60) Provisional application No. 61/932,386, filed on Jan. 28, 2014.

(51) Int. Cl.
*A61B 5/0215*    (2006.01)
*A61B 34/20*    (2016.01)
(Continued)

(52) U.S. Cl.
CPC ............ *A61B 34/20* (2016.02); *A61B 5/0538* (2013.01); *A61B 5/062* (2013.01); *A61B 5/068* (2013.01);
(Continued)

(58) Field of Classification Search
None
See application file for complete search history.

(56) References Cited

U.S. PATENT DOCUMENTS 4,476,872 A    10/1984  Perlin
4,762,135 A    8/1988   van der Puije et al.
(Continued)

FOREIGN PATENT DOCUMENTS

EP    0989384 A2    3/2000
EP    1772097       4/2007
(Continued)

OTHER PUBLICATIONS

CathPrint AB—Technology & Products; CathPrint Integrated catheter; http://cathprint.se/Technology/CompositeCatheterCathPrintIntegrated; pulled Aug. 21, 2014 (unaware of publication date).
(Continued)

*Primary Examiner* — Patricia J Park
(74) *Attorney, Agent, or Firm* — Dykema Gossett PLLC

(57) ABSTRACT

A medical device for the diagnosis or treatment of tissue in a body and method for fabricating the same are provided. The device includes an elongate, tubular, deformable shaft comprising a proximal end and a distal end. The device also includes an electronic subassembly (54) disposed within the shaft and a conductor (76, 78) coupled to and extending from the electronic subassembly. The electronic subassembly includes a flexible substrate (72) and an electronic device (74). The flexible substrate comprises an interior side
(Continued)

(84) and an exterior side (86) opposite the interior side. The flexible substrate also defines a first conductive area (92, 94). The electronic device is mounted on the interior side of the flexible substrate, is coupled to the first conductive area, and is at least partially enclosed within the flexible substrate.

32 Claims, 9 Drawing Sheets

(51) Int. Cl.
*A61B 5/053* (2006.01)
*A61B 18/14* (2006.01)
*A61B 5/06* (2006.01)
*B29C 65/48* (2006.01)
*A61B 34/30* (2016.01)
*B29L 31/00* (2006.01)

(52) U.S. Cl.
CPC .......... *A61B 18/1492* (2013.01); *B29C 65/48* (2013.01); *A61B 2034/2051* (2016.02); *A61B 2034/301* (2016.02); *A61B 2562/12* (2013.01); *A61B 2562/164* (2013.01); *B29L 2031/753* (2013.01)

(56) References Cited

U.S. PATENT DOCUMENTS

| | | | |
|---|---|---|---|
| 5,300,068 A | 4/1994 | Rosar et al. | |
| 5,343,860 A | 9/1994 | Metzger et al. | |
| 5,840,024 A | 11/1998 | Taniguchi et al. | |
| 5,840,031 A | 11/1998 | Crowley | |
| 5,964,705 A | 10/1999 | Truwit et al. | |
| 6,210,339 B1 | 4/2001 | Kiepen | |
| 6,233,476 B1 | 5/2001 | Strommer et al. | |
| 6,357,447 B1 | 3/2002 | Swanson et al. | |
| 6,498,944 B1 | 12/2002 | Ben-Haim et al. | |
| 6,569,162 B2 | 5/2003 | He | |
| 6,690,963 B2 | 2/2004 | Ben Haim et al. | |
| 6,788,967 B2 | 9/2004 | Ben Haim et al. | |
| 7,197,354 B2 | 3/2007 | Sobe | |
| 7,229,437 B2 | 6/2007 | Johnson et al. | |
| 7,263,397 B2 | 8/2007 | Hauck et al. | |
| 7,304,373 B2 | 12/2007 | Taggart et al. | |
| 7,386,339 B2 | 6/2008 | Strommer et al. | |
| 7,536,218 B2 | 5/2009 | Govari et al. | |
| 7,625,617 B1 | 12/2009 | Anderson et al. | |
| 7,686,802 B2 | 3/2010 | Stevens-Wright | |
| 8,147,486 B2 | 4/2012 | Honour et al. | |
| 8,221,408 B2 | 7/2012 | Johnson et al. | |
| 8,295,902 B2 | 10/2012 | Salahieh et al. | |
| 8,467,844 B2 | 6/2013 | Rea et al. | |
| 2002/0080233 A1 | 6/2002 | Irion et al. | |
| 2002/0167308 A1 | 11/2002 | Davis | |
| 2003/0187347 A1 | 10/2003 | Nevo et al. | |
| 2003/0195406 A1 | 10/2003 | Jenkins et al. | |
| 2004/0260241 A1 | 12/2004 | Yamamoto et al. | |
| 2005/0060885 A1 | 3/2005 | Johnson | |
| 2005/0065508 A1 | 3/2005 | Johnson et al. | |
| 2005/0085716 A1 | 4/2005 | Hamm et al. | |
| 2006/0091508 A1 | 5/2006 | Taggart et al. | |
| 2007/0060833 A1 | 3/2007 | Hauck | |
| 2007/0085528 A1 | 4/2007 | Govari et al. | |
| 2007/0219551 A1 | 9/2007 | Honour | |
| 2009/0143651 A1 | 6/2009 | Kallback et al. | |
| 2009/0171274 A1 | 7/2009 | Harlev | |
| 2009/0227885 A1 | 9/2009 | Lowery et al. | |
| 2009/0247942 A1 | 10/2009 | Kirschenman | |
| 2009/0247944 A1 | 10/2009 | Kirschenman et al. | |
| 2009/0247993 A1 | 10/2009 | Kirschenman et al. | |
| 2009/0248042 A1 | 10/2009 | Kirschenman et al. | |
| 2010/0022950 A1 | 1/2010 | Anderson et al. | |
| 2010/0094279 A1 | 4/2010 | Kauphusman | |
| 2010/0228112 A1 | 9/2010 | von Malmborg | |
| 2010/0256558 A1 | 10/2010 | Olson et al. | |
| 2010/0262040 A1 | 10/2010 | von Malmborg | |
| 2010/0318019 A1 | 12/2010 | Nee et al. | |
| 2011/0015569 A1 | 1/2011 | Kirschenman et al. | |
| 2011/0066029 A1* | 3/2011 | Lyu | A61M 25/0133 600/424 |
| 2012/0029504 A1 | 2/2012 | Afonso et al. | |
| 2012/0143298 A1 | 6/2012 | Just | |
| 2012/0172696 A1 | 7/2012 | Kallback et al. | |
| 2012/0172761 A1 | 7/2012 | Meller et al. | |
| 2012/0172842 A1 | 7/2012 | Sela et al. | |
| 2013/0066193 A1 | 3/2013 | Olson et al. | |
| 2013/0066194 A1 | 3/2013 | Seter et al. | |
| 2013/0169272 A1 | 7/2013 | Eichler et al. | |
| 2013/0172715 A1 | 7/2013 | Just | |
| 2013/0184549 A1 | 7/2013 | Avitall et al. | |
| 2014/0005508 A1 | 1/2014 | Estes et al. | |
| 2014/0030122 A1 | 1/2014 | Ozaki et al. | |
| 2014/0088591 A1 | 3/2014 | Just | |
| 2014/0142409 A1 | 5/2014 | Garcia et al. | |

FOREIGN PATENT DOCUMENTS

| | | |
|---|---|---|
| EP | 2208456 | 7/2010 |
| EP | 2032201 | 4/2013 |
| JP | H05115436 A | 5/1993 |
| JP | H06178757 A | 6/1994 |
| JP | 2008237732 A | 10/2008 |
| JP | 2011200340 A | 10/2011 |
| WO | 0232497 A1 | 4/2002 |
| WO | 2007139479 | 12/2007 |
| WO | 2009120982 | 10/2009 |
| WO | 2010129661 A1 | 11/2010 |
| WO | 2011005165 | 1/2011 |
| WO | 2011031201 | 3/2011 |
| WO | 2012177807 A1 | 12/2012 |
| WO | 2013074036 | 5/2013 |

OTHER PUBLICATIONS

CathPrint AB—Technology & Products; CathPrint Prefab Options; http://cathprint.se/Technology/prefab-2; pulled Aug. 21, 2014 (unaware of publication date).

CathPrint AB—Technology & Products; CathPrint catheter; http://cathprint.se/Technology/SimpleCatheterCathPrint; pulled Aug. 21, 2014 (unaware of publication date).

"Cathprint AB", Technology Brochure—A New Catheter & Endoscopic Paradigm. Publication date unknown. CathPrint AB, Stockholm, Sweden.

\* cited by examiner

MEDICAL DEVICE WITH A PACKAGED ELECTRONIC SUBASSEMBLY AND METHOD FOR FABRICATING THE SAME

CROSS-REFERENCE TO RELATED APPLICATIONS

This application claims the benefit of U.S. provisional application No. 61/932,386, filed 28 Jan. 2014, which is hereby incorporated by reference as though fully set forth herein.

BACKGROUND a. Field

This disclosure relates to a medical device for diagnosis or treatment of tissue in a body and method for fabricating the same. In particular, the instant disclosure relates to a medical device with a packaged electronic subassembly and method for fabricating the same.

b. Background Art

A wide variety of medical devices are inserted into the body to diagnose and treat various medical conditions. Catheters, for example, are used to perform a variety of tasks within human bodies and other bodies including the delivery of medicine and fluids, the removal of bodily fluids and the transport of surgical tools and instruments. In the diagnosis and treatment of atrial fibrillation, for example, catheters may be used to deliver electrodes to the heart for electrophysiological mapping of the surface of the heart and to deliver ablative energy to the surface among other tasks.

It is known to determine the position of such medical devices through the use of an electromagnetic field-based positioning system, which, in turn, typically involves equipping the medical device with an electromagnetic field sensing sensor. Such a sensor is then connected to a conductor in an electrical cable in the medical device to transfer the detected signal to the positioning system for further processing. Such an electrical connection can be made my soldering the respective leads of the sensor and cable together at a solder joint. However, the leads and sensors themselves are delicate and, thus, can be damaged during fabrication and assembly of the medical device. Moreover, due to the small diameter (e.g., 10 μm) and fragility of the leads, the leads can break at or near the solder joint during or after testing (e.g., stress rupture testing) of the medical device. Another mechanism for electrically coupling the sensor and cable is by coupling the respective leads of the sensor and cable to a rigid or flexible substrate disposed therebetween. In light of the relatively small dimensions that such sensors must exhibit in order to fit into a typical medical device, fabrication of such sensors can be complicated, occupy undesirable amounts of radial space in the device, and/or involve fabrication methods that are more costly than desired.

The foregoing discussion is intended only to illustrate the present field and should not be taken as a disavowal of claim scope.

BRIEF SUMMARY

Among other things, various embodiments disclosed herein are directed to a medical device for diagnosis or treatment of tissue in a body and a method for fabricating the same. In particular, the instant disclosure relates to a medical device with a packaged electronic subassembly and method for fabricating the same.

A medical device for the diagnosis or treatment of tissue in a body in accordance with one embodiment of the present teachings includes an elongate, tubular, deformable shaft comprising a proximal end and a distal end. The device also includes an electronic subassembly disposed within the shaft and a conductor coupled to and extending from the electronic subassembly. The electronic subassembly includes a flexible substrate and an electronic device. The flexible substrate comprises an interior side and an exterior side opposite the interior side. The flexible substrate also defines a first conductive area. The electronic device is mounted on the interior side of the flexible substrate, is coupled to the first conductive area, and is at least partially enclosed within the flexible substrate.

A method for fabricating a medical device for diagnosis or treatment of tissue in a body in accordance with another embodiment of the present teachings includes providing a flexible substrate. The flexible substrate comprises an interior side, an exterior side opposite the interior side, and first and second edges extending between the interior and exterior sides. The flexible substrate also defines a first conductive area. The method further includes mounting an electronic device on the interior side of the flexible substrate and coupling the electronic device to the first conductive area. The method further includes deforming the flexible substrate so as to at least partially enclose the electronic device. The method further includes inserting the flexible substrate into an elongate, tubular, deformable shaft comprising a proximal end and a distal end and electrically coupling a conductor to the electronic device.

A medical device for diagnosis or treatment of tissue in a body in accordance with another embodiment of the present teachings includes an elongate, tubular, deformable shaft comprising a proximal end and a distal end. The medical device further includes an electronic subassembly disposed within the shaft. The electronic subassembly includes a flexible substrate comprising a first side and a second side opposite the first side with the flexible substrate defining a first conductive area. The electronic subassembly further includes an electronic device mounted on the first side of the flexible substrate and coupled to the first conductive area. The medical device further includes a conductor comprising a distal end coupled to and extending proximally from the electronic subassembly. A surface area of the first conductive area is greater than a surface area of the distal end of the conductor.

A medical device and method for making the same in accordance with the present teachings is advantageous relative to conventional devices and methods. A medical device and method for making the same in accordance with the present teachings provide a more robust and compact sensor and a reliable connection between the sensor and proximally-extending cable, all while maintaining or improving the functionality of the device. In addition, the method for making the device is less complex and less expensive than conventional methods and results in smaller failure rates during post-fabrication testing.

The foregoing and other aspects, features, details, utilities, and advantages of the present teachings will be apparent from reading the following description and claims, and from reviewing the accompanying drawings.

DETAILED DESCRIPTION

Various embodiments are described herein of various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a physician manipulating one end of an instrument used to treat a patient. The term "proximal" refers to the portion of the instrument closest to the physician and the term "distal" refers to the portion located furthest from the physician. Similarly, "more proximal" means closer to the physician whereas "more distal" means further form the physician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Figure 1:
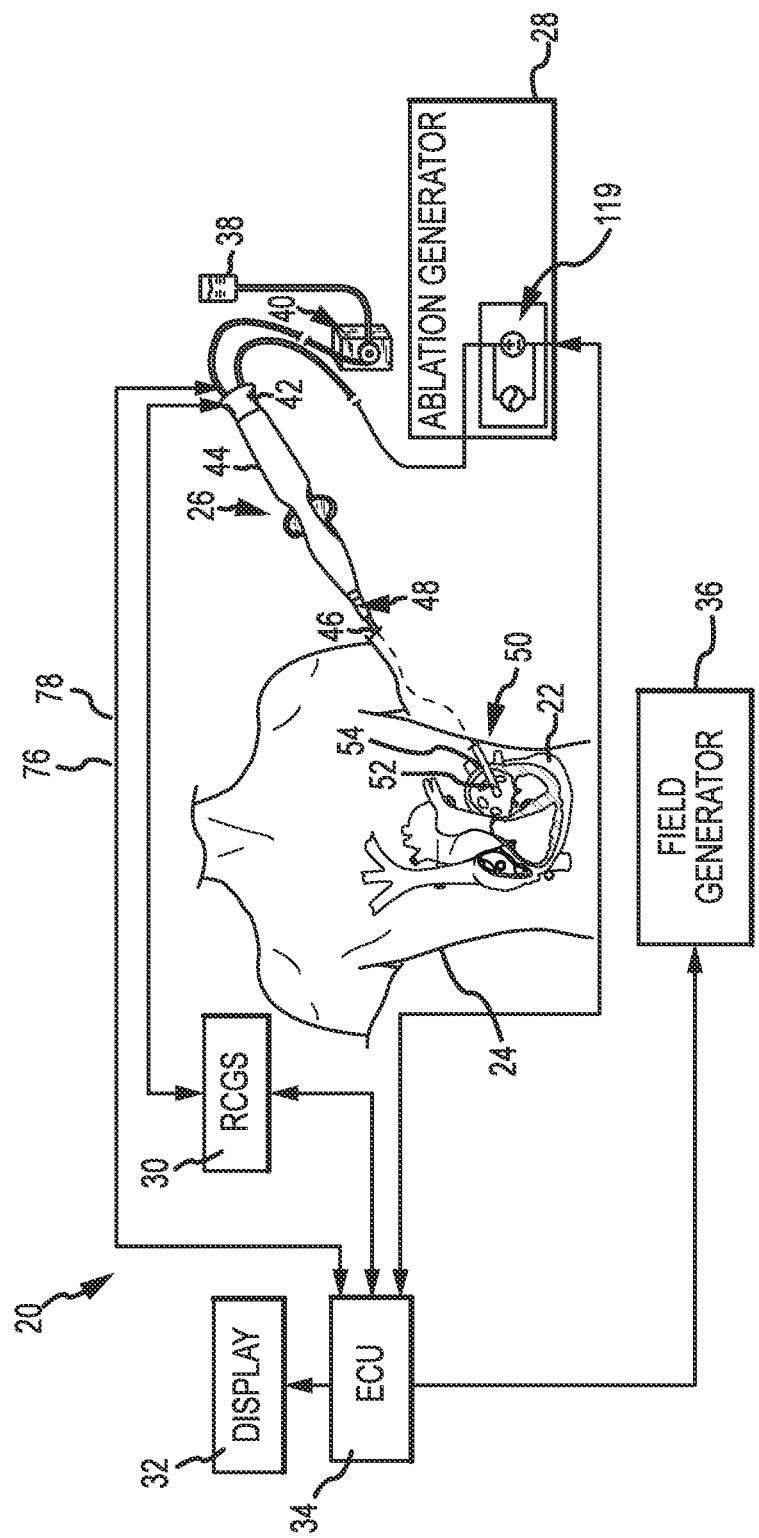
FIG. 1 is diagrammatic view of one embodiment of a system for diagnosis or treatment of tissue in a body in accordance with one embodiment of the present teachings.

Referring now to the drawings wherein like reference numerals are used to identify identical components in the various views, FIG. 1 illustrates one embodiment of a system 20 for diagnosis or treatment of tissue 22 in a body 24. In the illustrated embodiment, tissue 22 comprises cardiac tissue within a human body. It should be understood, however, that a system 20 in accordance with the present teachings may find application in connection with procedures for the diagnosis or treatment of a variety of tissues in human and non-human bodies. System 20 includes a medical device for diagnosis or treatment of tissue 22. In accordance with one embodiment, system 20 includes a catheter 26 for diagnosis or treatment of tissue 22 and may further include an ablation generator 28, a remote catheter guidance system (RCGS) 30, a display system 32, an electronic control unit (ECU) 34, and an external field generator 36.

Figure 2:
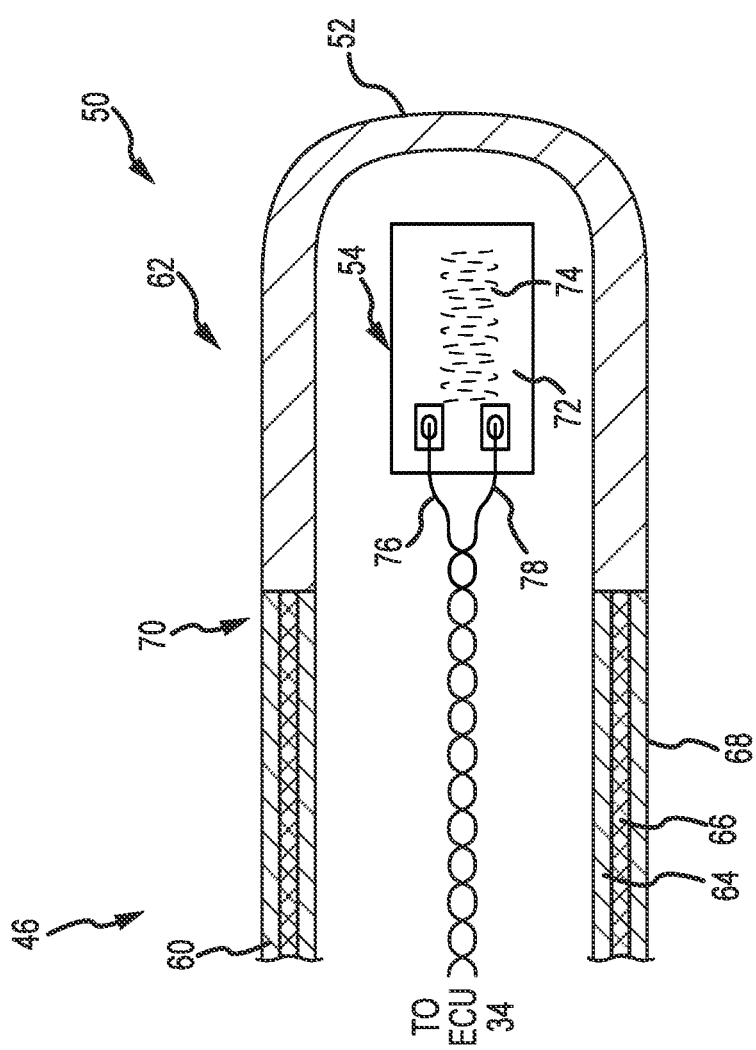
FIG. 2 is a sectional view of a portion of a medical device for diagnosis or treatment of tissue in accordance with one embodiment of the present teachings.

Catheter 26 is provided for examination, diagnosis and treatment of internal body tissues such as tissue 22. In accordance with one embodiment of the present teachings, catheter 26 comprises an ablation catheter and, more particularly, an irrigated radio-frequency (RF) ablation catheter. It should be understood, however, that catheter 26 is provided for illustration only and that system 20 could be adapted for use with other types of catheters including electrophysiology (EP) mapping catheters and intracardiac echocardiograph (ICE) catheters, as well as for use with other types of ablation catheters including those providing different types of ablation energy (e.g., cryoablation, ultrasound, laser, microwave, electroporation, etc.). Further, it should be understood that system 20 can be adapted for use with other types of medical devices used in the diagnosis or treatment of tissue 22 including, for example, introducer sheaths. In the illustrated embodiment, catheter 26 may be connected to an irrigant fluid source 38 having a biocompatible fluid such as saline which is passed through an irrigation pump 40 (which may comprise, for example, a fixed rate roller pump or variable volume syringe pump with a gravity feed supply from fluid source 38 as shown) for irrigation. Catheter 26 may also be electrically connected to ablation generator 28 for delivery of ablating RF energy. Catheter 26 may include a cable connector or interface 42, a handle 44, a flexible shaft 46 having a proximal end 48 and a distal end 50, and one or more ablation and sensing electrodes 52. Referring to FIG. 2, in accordance with certain aspects of the present teachings, catheter 26 may further include an electronic subassembly 54 and conductors 56, 58 electrically connecting electronic subassembly 54 with ECU 34. Catheter 26 may also include other conventional components not illustrated herein such as a temperature sensor, additional pacing or mapping electrodes, and corresponding conductors or leads.

Referring again to FIG. 1, connector 42 provides mechanical, fluid and electrical connection(s) for cables extending from ablation generator 28, RCGS 30, and pump 40. Connector 42 may be disposed at proximal end 48 of catheter 26. Although directly attached to handle 44 in the illustrated embodiment, connector 42 may be coupled to handle 44 indirectly through, for example, several feet of cable.

Handle 44 provides a location for the physician to hold catheter 26 and may further provides means for steering or guiding shaft 46 within body 24. For example, handle 44 may include means to change the length of a steering wire extending through catheter 26 to distal end 50 of shaft 46 to control translation and/or deflection of the distal end 50 of shaft 46 to steer shaft 46. Handle 44 may be manipulated manually by a physician or automatically through, for example, robotic controls such as RCGS 30. It should be understood that the construction of handle 44 may vary and may be absent in a fully-robotic implementation of the system.

Shaft 46 provides structural support to other components of catheter 26 including electrodes 52, electronic subassembly 54, conductors 56, 58 extending to electronic subassembly 54, and other conductors and wires extending to electrodes 52 and electronic subassembly 54 (and possibly additional electronics used for signal processing or conditioning). Shaft 46 may also permit transport, delivery, and/or removal of fluids (including irrigation fluids and bodily fluids), medicines, and/or surgical tools or instruments. Shaft 46 is configured to be received within body 24 and may be introduced into a blood vessel or other structure within body 24 through an introducer. Shaft 46 may then be steered or guided through body 24 to a desired location such as tissue 22 with a guiding introducer such as the Agilis™ NxT steerable introducer available from St. Jude Medical, Inc., with RCGS 30, and/or with guide wires, pullwires or other means known in the art.

Referring to FIG. 2, shaft 46 may include an elongate, tubular member 60 and a tip 62. Member 60 is flexible or deformable and configured for movement within body 24 (FIG. 1). Member 60 also defines one or more lumens configured to house conductors 76, 78 and steering wires and to allow fluids to pass therethrough. Member 60 may include a tubular, polymeric inner liner 64, a braided wire layer 66 for torque transfer, and an outer polymeric jacket 68. Liner 64 may be made from a polymeric material such as polyfluoroethylene (PTFE) including PTFE sold under the registered trademark "TEFLON" by E.I. DuPont de Nemours & Co. Corp, polyether block amides, nylon or thermoplastic elastomers such as the elastomer sold under the registered trademark "PEBAX" by Arkema, Inc. Braided wire layer 66 is configured to provide appropriate levels of pushability, torqueability, flexibility, and kink resistance to shaft 46. Layer 66 may be formed from stainless steel wire, and may be flat wire (wire having a cross-section that, when taken along the wire's longitudinal axis and measured along two orthogonal axes, is substantially rectangular) arranged in various braid patterns including one-over-one (involving at least two wires) or two-over-two (involving at least four wires) crossover patterns. The wire may be coated with a layer of an insulating material. The wire braid may be directly wound about liner 64 or placed on a core that is slid over liner 64. Jacket 68 is made from a polymeric material such as polyfluoroethylene (PTFE) including PTFE sold under the registered trademark "TEFLON" by E.I. DuPont de Nemours & Co. Corp, polyether block amides, nylon or thermoplastic elastomers such as the elastomer sold under the registered trademark "PEBAX" by Arkema, Inc. and may be extruded over layer 66. Additional details regarding several exemplary catheter constructions may be found in commonly assigned U.S. Pat. No. 7,914,515, the entire disclosure of which is incorporated herein by reference. Tip 62 may be received at a distal end 70 of member 60. Tip 62 may be made from a material or materials that are relatively rigid and may comprise, or may be configured to support, an electrode 52.

Referring again to FIG. 1, electrodes 52 on the outer surface of member 60 or tip 62 are provided for a variety of diagnostic and therapeutic purposes including, for example, electrophysiological studies, catheter identification and location, pacing, and cardiac mapping and ablation. In the illustrated embodiment, catheter 26 includes ablation tip electrode 52 at distal end 50 of shaft 46 that functions as a radio-frequency ablation delivery element. Catheter 26 may also include one or more ring electrodes (not shown) proximal of tip electrode 52 that may be used to obtain electrograms for tissue 22 and for other conventional purposes. It should be understood, however, that the number, orientation, and purpose of electrodes 52 may vary. Electrodes 52 may be made from various electrically conductive materials including those containing gold, platinum, iridium, palladium, rhodium, stainless steel, and/or any combination thereof.

Referring again to FIG. 2, electronic subassembly 54 is provided to perform any of a variety of functions performed by electronic components in a given medical device. In accordance with one embodiment of the present teachings, electronic subassembly 54 may be provided for use in determining the position of catheter 26, and particularly distal end 50 or tip 62 of catheter 26. Subassembly 54 may alternatively be used to perform various functions associated with ablation catheter 26 including, for example, controlled delivery of ablation current to a tip electrode, electrogram sensing, temperature sensing, and signal processing or conditioning. It should further be understood that the functionality of subassembly 54 will depend on the nature of the medical device and that subassembly 54 may therefore perform different functions where the device is not an ablation catheter. Although one electronic subassembly 54 is shown in the illustrated embodiment, it should be understood that multiple electronic subassemblies 54 may be used to perform the same, related, or different functions within catheter 26. In the illustrated embodiment, subassembly 54 is illustrated as being disposed in the distal portion 50 of shaft 46. Alternatively, electronic subassembly 54 can be disposed in any portion of shaft 46 (including in an orifice in tip 62 or onto structure forming a lumen within shaft 46 proximal to tip 62). Subassembly 54 may include a flexible substrate 72, one or more electronic devices 74 mounted on substrate 72 and one or more conductors 76, 78 extending from substrate 72.

Figure 3:
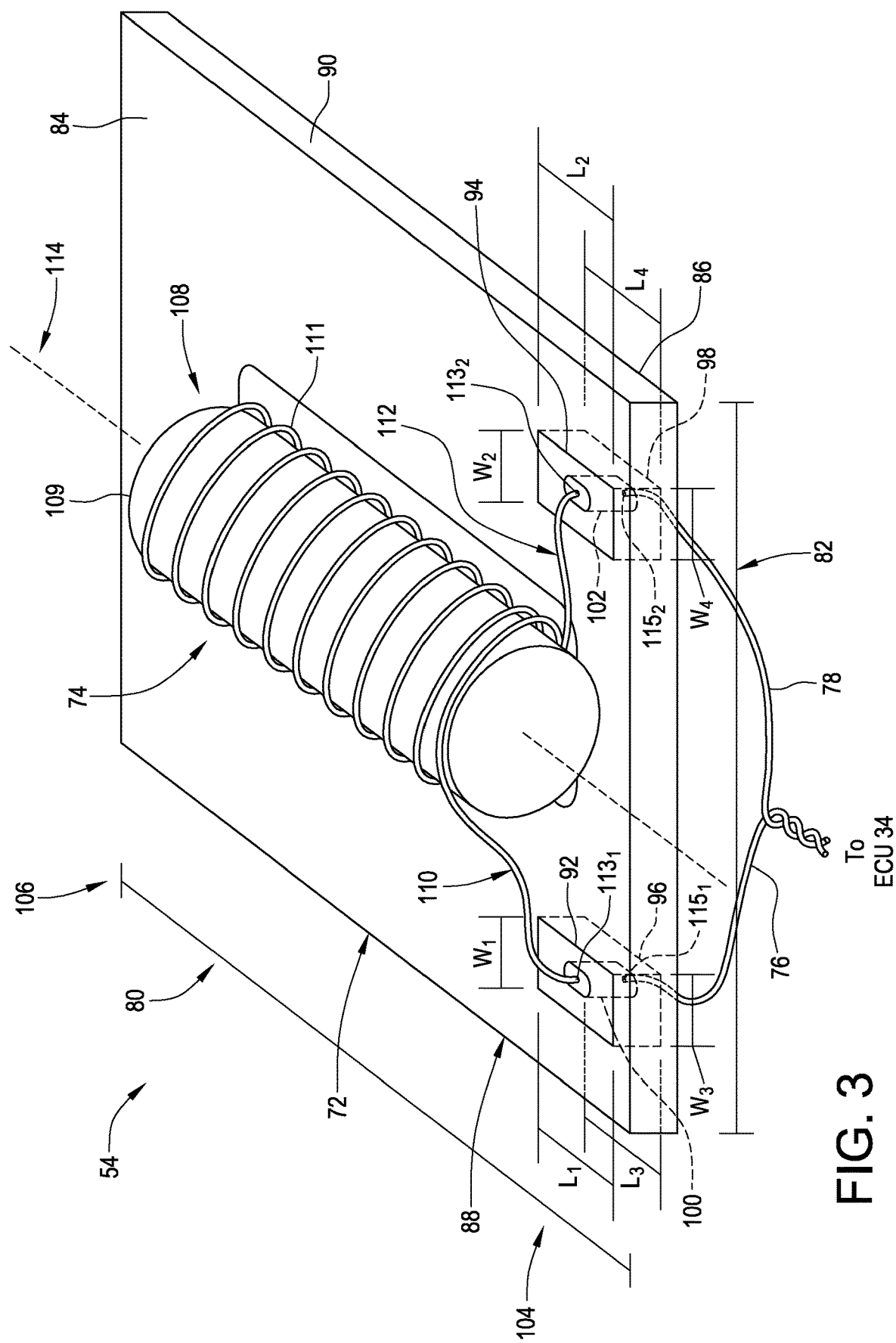
FIG. 3 is a perspective view of a partially formed electronic subassembly of the medical device of FIG. 2 in accordance with one embodiment of the present teachings.

Flexible substrate 72 provides structural support and serves as a mechanical and electrical connector for device 74 and conductors 76, 78. Substrate 72 may be made from any insulative and relatively flexible material, such as polyimides, polyethylene terephthalate (PET), and/or polyethylene naphthalate (PEN), such as those sold under the trademarks Tetoron®, Teonex®, and Melinex® and generally available from DuPont Tejin Films. Such materials, e.g., PEN, may be able to withstand high process temperatures without being adversely affected and may be relatively thin, which may improve handleability and quality. Referring to FIG. 3, in one state, substrate 72 may be generally rectangular in shape and have a length 80 and a width 82. Substrate 72 may define opposite sides 84, 86 with side 84 comprising an interior side and side 86 comprising an exterior side upon final assembly as described hereinbelow. Substrate 72 may further define edges extending between sides 84, 86, including edges 88, 90 disposed on opposite sides of substrate 72. Edges 88, 90 may be perpendicular to sides 84, 86, or extend at a non-perpendicular angle between sides 84, 86. Substrate 72 may define one or more conductive areas 92, 94 or contact pads, on interior side 84 and one or more conductive areas 96, 98 on exterior side 86. Substrate 72 may further define conductive paths 100, 102 between conductive areas 92, 96 and 94, 98, respectively. In the illustrated embodiment, conductive areas 92, 94, 96, 98 are disposed at a proximal end 104 of substrate 72. It should be understood, however, that one or more of conductive areas 92, 94, 96, 98 could be located at a distal end 106 of substrate 72 or at a location between ends 104, 106. Further, conductive areas 92, 94, 96, 98 may be disposed on any surface of substrate 72 including any edge extending between sides 84, 86. Also in the illustrated embodiment, conductive areas 92, 96, and 94, 98 are aligned such that conductive paths 100, 102, extend the shortest possible distance between areas 92, 96 and 94, 98, respectively. It should be understood, however, that areas 92, 94, 96, 98 could be located at various locations on substrate 72 with paths 100,102 taking a straight or circuitous route through substrate 72 to electrically couple areas 92, 94, and 96, 98 respectively. Conductive areas 92, 94, 96, 98 may be made from conductive materials such as copper and may have a surface finish such as electroless nickel/gold, silver, etc.

One of ordinary skill in the art will understand that conductive paths 100, 102 can be formed by (for example and without limitation) constructing through vias and/or blind vias through the flexible substrate 72. In one embodiment, conductive paths 100, 102 are formed by creating through vias between conductive areas 92, 96 and 94, 98 and filling the through vias with a conductive material, such as copper. Thus, conductive paths 100, 102 can be formed during the formation/manufacture of the flexible substrate 72 itself (e.g., during plating). In another embodiment, conductive paths 100, 102 are formed by laser-drilling through the flexible substrate 72 to conductive areas 92, 94 or 96, 98 and, thereafter, filling the drilled holes with conductive paste. The lead wires from device 74 and/or the conductors 76, 78 of cable 34 may be electrically connected to conductive paths 100, 102 and conductive areas 92, 94, 96, 98 during the curing of the conductive paste. In some embodiments, some or all of conductive areas 92, 94, 96, 98 can be made from conductive paste.

Device 74 is provided for use in determining the position of the distal portion of catheter 26 within a coordinate system and within body 24. As discussed hereinabove, however, the function of device 74 may vary depending on the nature of the medical device in which subassembly 54 is used. Further, although the illustrated embodiment shows a single device 74 on substrate 72, it should be understood that multiple devices 74 may be mounted to substrate 72. Device 74 may comprise an electromagnetic field detector and, particularly, a coil assembly 108 that includes a coil 111. When the distal tip 62 of catheter 26 is moved within a magnetic field, the current induced in coil 111 will vary and the coil 111 will generate a signal indicative of the position of tip 62 of catheter 26. Although a single coil 111 is shown in the illustrated embodiment, multiple coils may be mounted on substrate 72 or on different substrates as part of different subassemblies to provide a determination of the position of tip 62 of catheter 26 in three-dimensional space. The coil 111 may extend along the entire length 80 or width 82 of substrate 72 or only a portion of the length 80 or width 82. In the illustrated embodiment, the coil 111 is disposed in the center of substrate 72, but it should be understood that the location of the coil 111 on substrate 72 may vary. The coil 111 may comprise a continuous wire wound in a helix. Coil assembly 108 may further include a magnetic core 109 about which the coil 111 may be wrapped. The coil assembly 108 may include leads 110, 112 at either or both ends of coil 111. The axial ends of leads 110, 112 may be coupled to conductive areas 92, 94, respectively, by soldering and may each have a surface area $113_1$, $113_2$, respectively. Coil assembly 108 may further be mounted to substrate 72 by using an adhesive such as a nonconductive epoxy or polyurethane on one or both of substrate 72 and coil 108 and curing the adhesive in an oven.

Conductors 76, 78 are provided to transfer electrical signals among components within catheter 26 and, in particular, between device 74 and ECU 34 or other signal processing and conditioning circuits. Conductors 76, 78 may comprise wires or cables connected to and extending from substrate 72 to proximal end 48 of shaft 46. Alternatively, conductors 76, 78 may comprise printed traces formed on the surface of a lumen extending through shaft 46 as discussed in greater detail in co-pending and commonly owned U.S. Patent Application No. 61/932,499 filed Jan. 28, 2014 (hereinafter the '499 application), which is hereby incorporated by reference in its entirety as though fully set forth herein.

Figure 4:
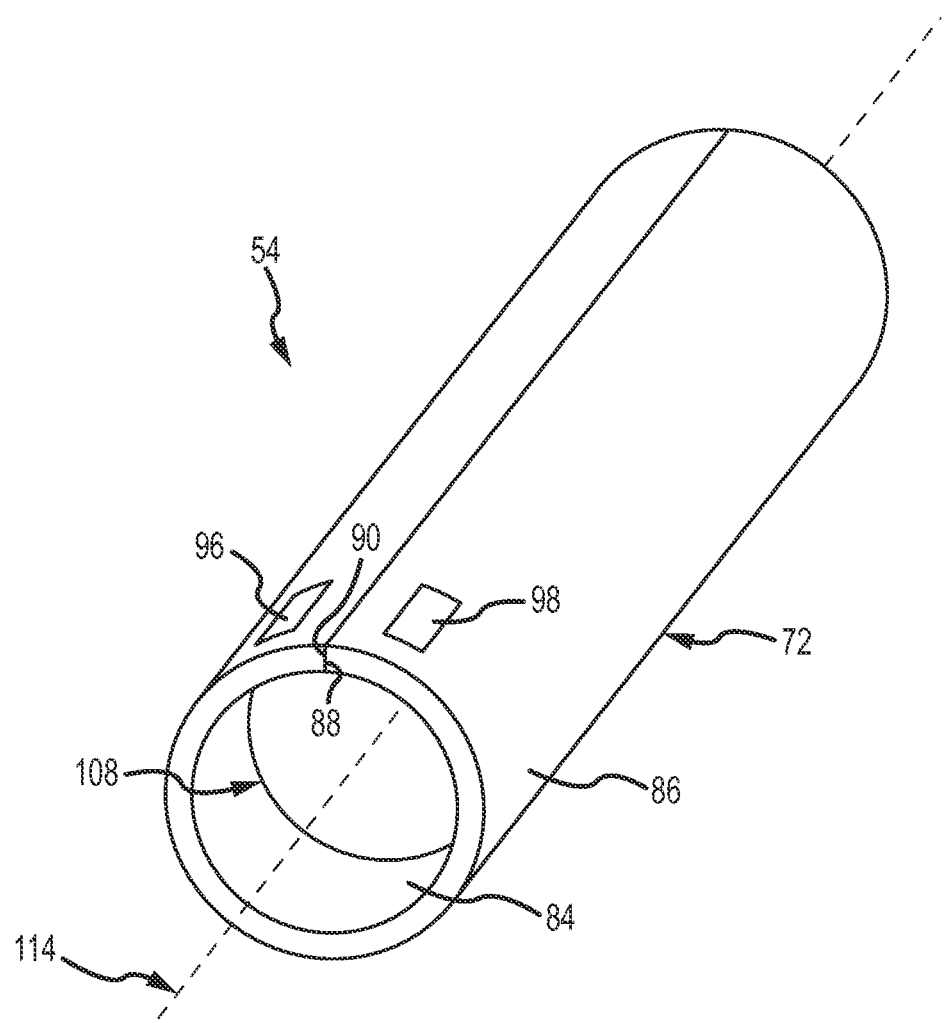
FIG. 4 is a perspective view of the electronic subassembly of FIG. 3 in a deformed state.

Referring now to FIG. 4, assembly 54 is shown in a deformed state. Due to its flexibility, flexible substrate 72 can be deformed. In accordance with one embodiment, substrate 72 is deformed about an axis, such as longitudinal axis 114, and shaped into a cylinder that at least partially encloses and, in the illustrated embodiment, circumferentially surrounds, device 74. In other embodiments, substrate 72 may be deformed in a manner that is not axisymmetric and/or not about an axis (longitudinal or otherwise). In the illustrated embodiment, edges 88, 90 are brought together and bonded with an adhesive such as an ultraviolet cure adhesive. It should be understood that flexible substrate 72 could alternatively be deformed by bringing the edges extending between edges 88, 90 together such that substrate 72 is deformed about an axis perpendicular to axis 114 and would surround the axial ends of coil assembly 108. Further, although the illustrated embodiment shows edges 88, 90, aligned along their lengths such that the end face of substrate 72 is annular in shape, it should be understood that edges 88, 90 may only partially overlap such that the end face of substrate 72 takes on a more helical shape. In an alternative embodiment, substrate 72 may be deformed such that edges 88, 90 extend past one another and a portion of sides 84, 86 overlap. In such an embodiment, the bonding would occur in the overlapped area between sides 84, 86, and conductive paths 100, 102 may extend into and/or through the overlapped area. Substrate 72 can also be deformed into various shapes and formations, such as a cone. For example and without limitation, substrate 72 can be deformed by folding substrate 72 (at least partially) over device 74. Furthermore, substrate 72 can be deformed and/or folded any number of times to at least partially enclose device 74. Because substrate 72 at least partially encloses device 74, substrate 72 protects device 74 from external forces and provides a more robust subassembly 54. Further, conductive areas 92, 94, 96, 98 remain easily accessible for connection thereto by device 74 and conductors 76, 78.

As best shown in FIG. 3, conductors 76, 78 may each have a distal axial end (for connection to subassembly 54), each end with its own surface area $115_1$, $115_2$, respectively. In an embodiment, conductive areas 92, 94, 96, 98 each have surface areas (i.e., the areas exposed on sides 84, 86 which may be defined by the product of a length $L_{1-4}$ and a width $W_{1-4}$) that are greater than the surface areas $115_1$, $115_2$ of the distal axial ends of conductors 76, 78 and the surface areas $113_1$, $113_2$ of the axial ends of leads 110, 112 of coil assembly 108 (e.g., to strengthen the respective bonds). Although the flexible substrate 72 is illustrated as being deformed to at least partially enclose electronic subassembly

54, one of ordinary skill in the art would understand that the substrate 72 may be pre-formed (e.g., by extrusion) to assure a shape that will at least partially enclose subassembly 54 upon assembly. In such an embodiment, substrate 72 may be a unitary structure without joints between portions of substrate 72. Furthermore, one of ordinary skill in the art would understand that the flexible substrate 72 may not be deformed and/or that the electronic subassembly 54 may not be enclosed. For example and without limitation, the flexible substrate 72 may remain undeformed as illustrated in the embodiment of FIG. 3.

Figure 5:
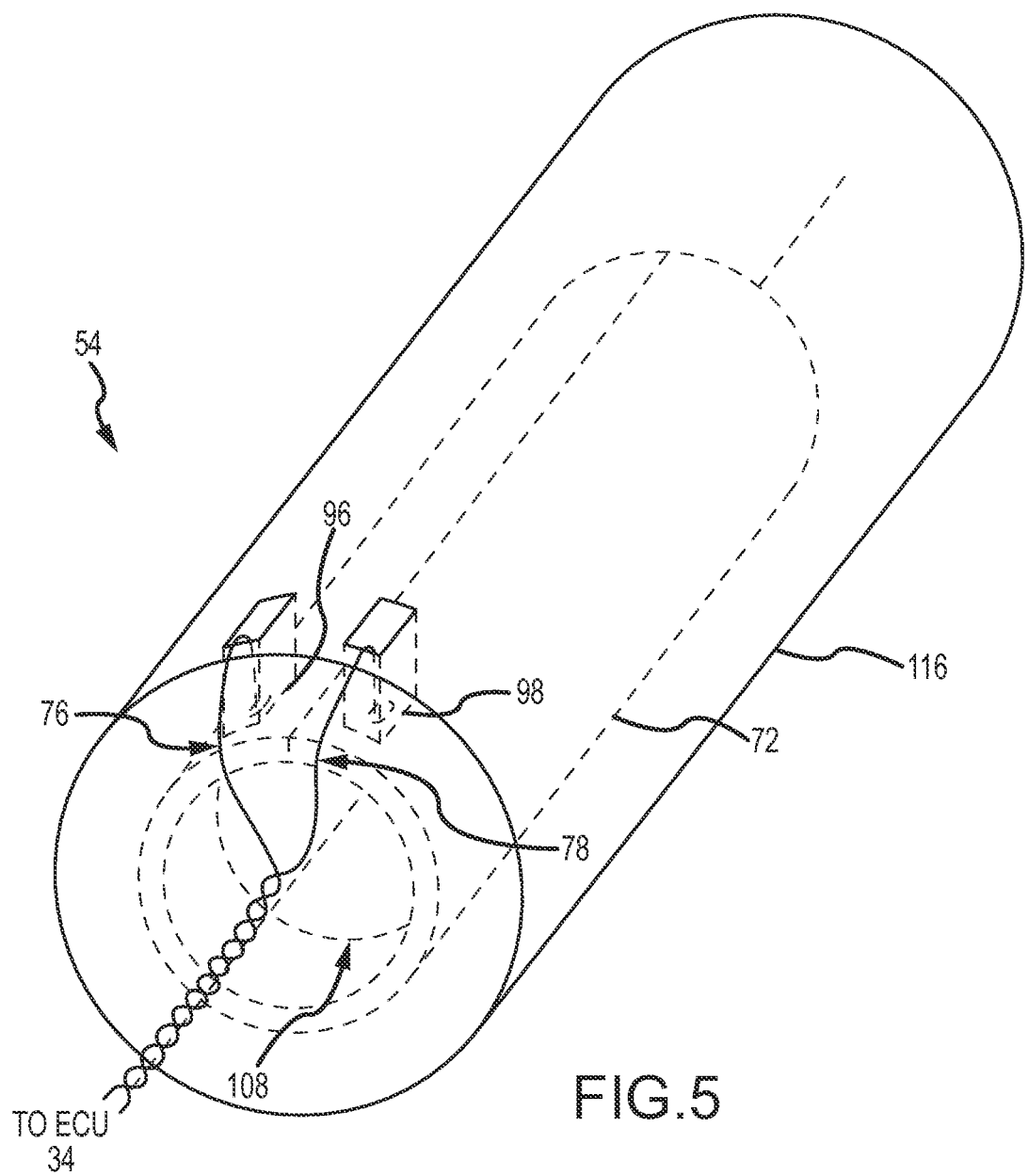
FIG. 5 is a perspective view of the electronic subassembly of FIG. 4 in an encapsulated state.

Referring now to FIG. 5, subassembly 54 is shown in an encapsulated state. One of ordinary skill in the art would understand that encapsulation is optional and that electronic subassembly 54 may remain unencapsulated as illustrated in FIG. 4. In one embodiment, subassembly 54 may be encapsulated with an electronics molding compound 116. Because electronics molding compounds 116 are silica-filled thermoset resin systems, they provide high material strength and durability, thermal conductivity, and resistance to dielectric breakdown. Therefore, compound 116 provides more protection and robustness for post-encapsulation processing and assembly. In another embodiment, subassembly 54 may be encapsulated via a method known to one of ordinary skill in the art as "glob top." In the "glob top" embodiment, a drop of epoxy or resin may be deposited on the top of subassembly 54 before or after conductors 76, 78 are connected to conductive areas 96, 98. The encapsulant used in the "glob top" method may have a high viscosity (to allow the material to flow through and around subassembly 54) and may be a "chip-on-board (COB) encapsulant", such as (for example and without limitation) those sold under the trademarks Masterbond® and EpoTek® and/or those generally available from Henkel AG & Co. KGaA, Master Bond Inc., Epoxy Technology, Inc., AI Technology, Inc., Shin-Etsu Chemical Co., Ltd., NAMICS Corporation, Zymet Inc., and Hitachi Chemical Co., Ltd. It should be understood that other methods and/or alternative molding materials may be used to encapsulate subassembly 54, such as (for example and without limitation) silicone liquid injection molding (LIM) and insert injection molding using thermoplastic resins (e.g., polycarbonate). The desired thickness of compound 116 may also vary depending on the catheter size and desired protection of electronic subassembly 54. Additionally, encapsulated electronic subassembly 54 may be generally cylindrical in shape. However, encapsulated electronic assembly 54 may be shaped in a variety of forms. Following encapsulation, conductive areas 96, 98 may be exposed through compound 116 (or epoxy or resin in the "glob top" embodiment, for example) so that conductors 76, 78 may be connected thereto. Conductors 76, 78 may be soldered to conductive areas 96, 98 using reflowed solder paste.

Figure 6:
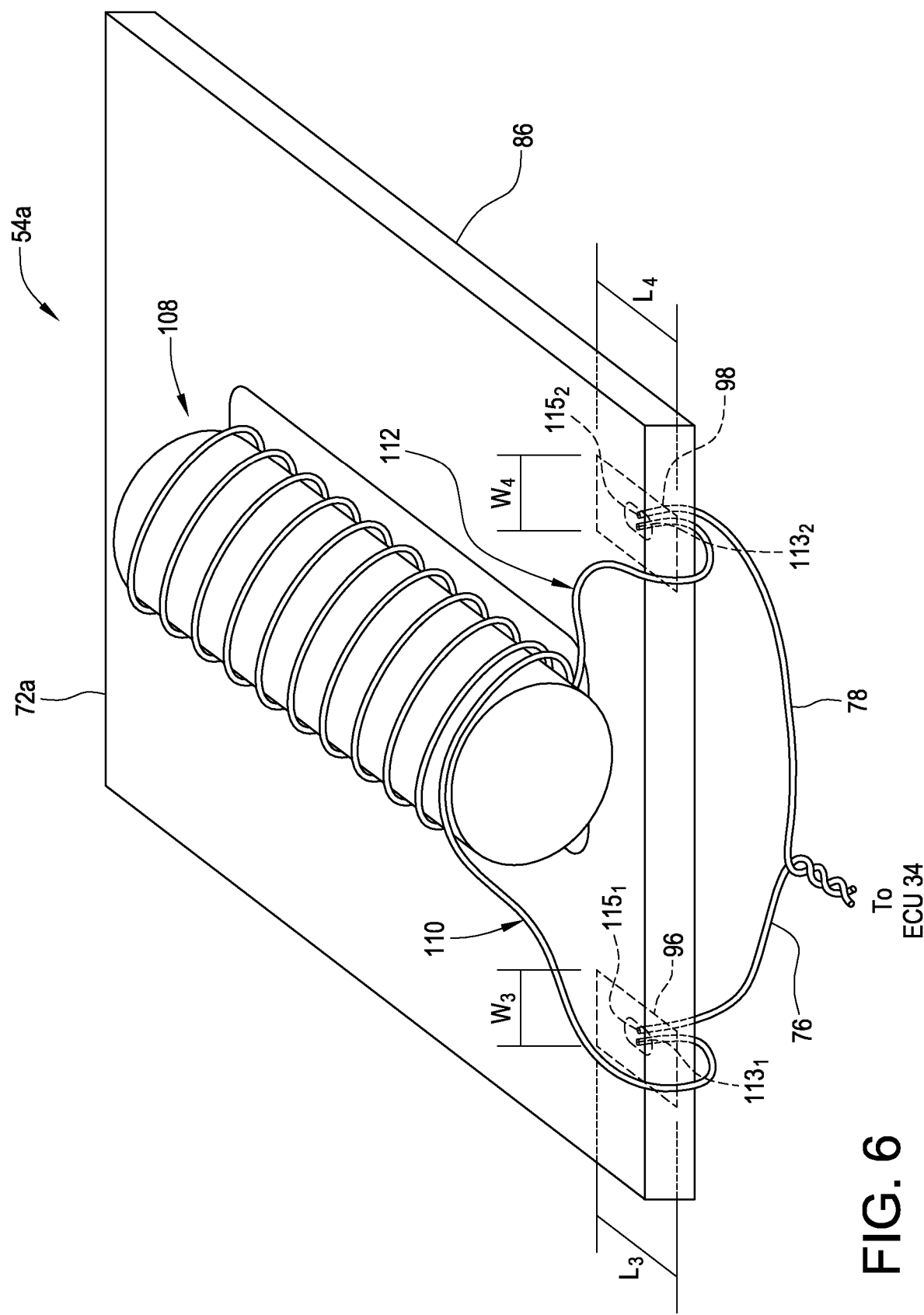
FIG. 6 is a perspective view of a partially formed electronic subassembly of the medical device of FIG. 2 in accordance with another embodiment of the present teachings.
Figure 7:
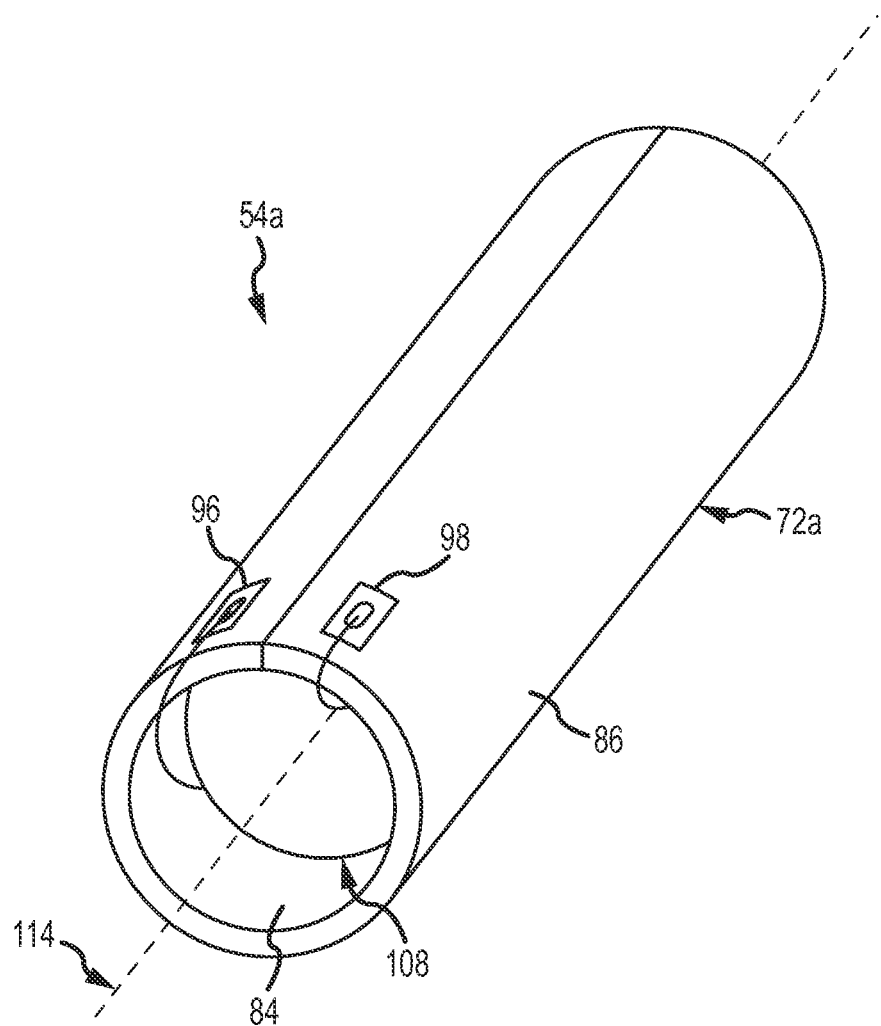
FIG. 7 is a perspective view of the electronic subassembly of FIG. 6 in a deformed state.
Figure 8:
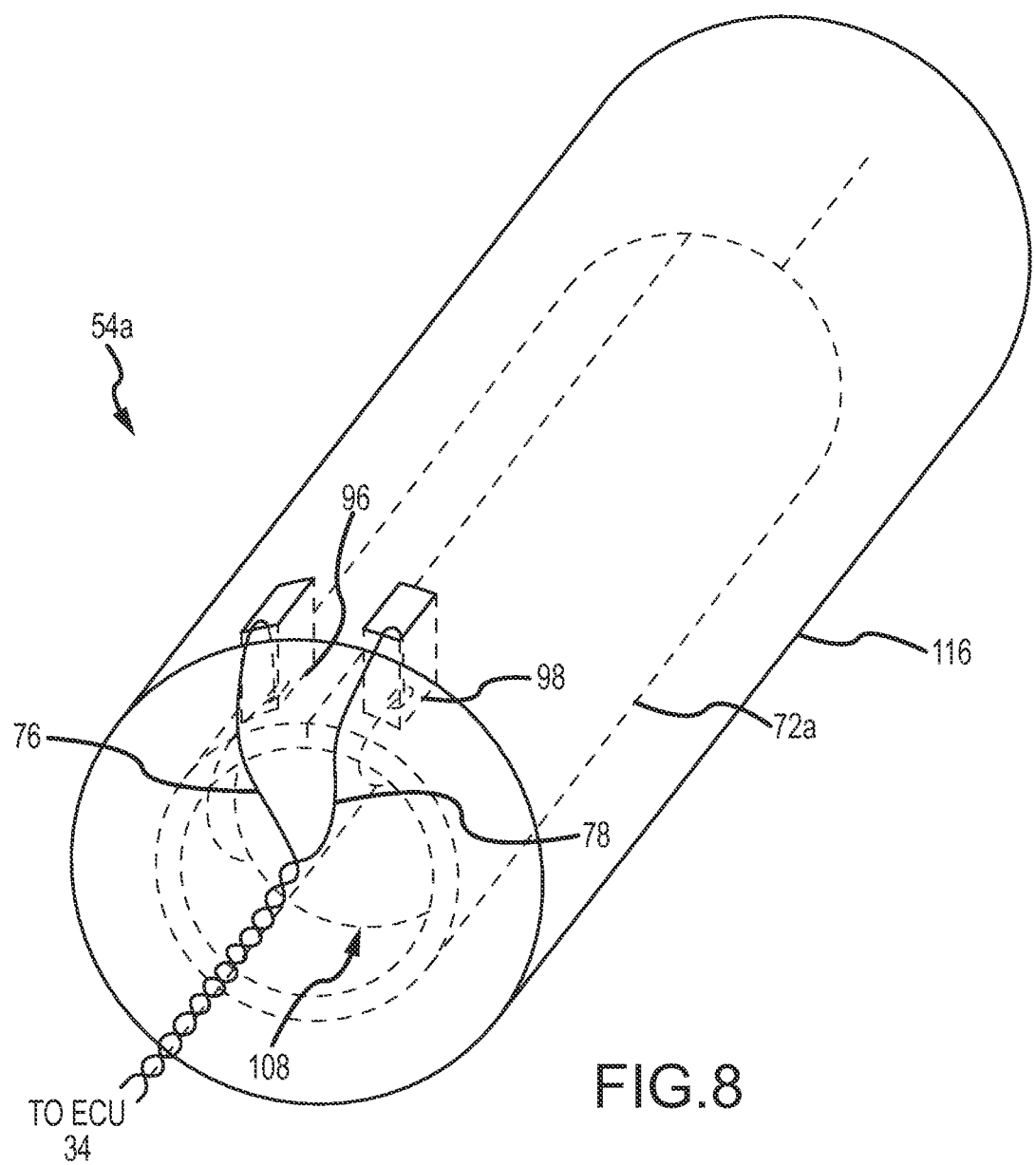
FIG. 8 is a perspective view of the electronic subassembly of FIG. 7 in an encapsulated state.

Referring now to FIGS. 6-8, an alternative embodiment of an electronic subassembly 54a is shown prior to deformation, in a deformed state and in an encapsulated state. As with the embodiments of FIGS. 3-5, deformation of flexible substrate 72a and encapsulation of subassembly 54a are optional. Subassembly 54a is similar to subassembly 54, but the leads 110, 112 of coil assembly 108 are connected to conductive areas 96, 98 on exterior side 86 of substrate 72a. Although leads 110, 112 are illustrated as extending around an edge of flexible substrate 72a, it should be understood that leads 110, 112 could alternatively extend through substrate 72a directly to conductive areas 96, 98 via bores in substrate 72a. Conductors 76, 78 are likewise connected to conductive areas 96, 98. As a result, subassembly 54a eliminates several conductive areas and conductive paths between areas found in substrate 72a of subassembly 54a.

Referring again to FIG. 1, ablation generator 28 generates, delivers and controls radiofrequency energy used by catheter 26. Generator 28 includes a radiofrequency generator 119 configured to generate an ablation signal that is output across a pair of source connectors: a positive polarity connector which may connect to electrode 52 on catheter 26; and a negative polarity connector which may be electrically connected by conductors or lead wires to a patch electrode (not shown) on body 24. It should be understood that the term connectors as used herein does not imply a particular type of physical interface mechanism, but is rather broadly contemplated to represent one or more electrical nodes. Generator 28 is configured to generate a signal at a predetermined frequency in accordance with one or more user-specified parameters (e.g., power, time, etc.) and under the control of various feedback sensing and control circuitry as is known in the art. Ablation generator 28 may also monitor various parameters associated with the ablation procedure including impedance, the temperature at the tip 62 of catheter 26, ablation energy, and the position of the catheter 26 and provide feedback to the physician regarding these parameters.

RCGS 30 may be provided to manipulate catheter 26. In particular, RCGS 30 permits control of translation, distal bending, and virtual rotation of catheter 26 and any surrounding sheath. RCGS 30 therefore provides the user with a type of control similar to that provided by conventional manually-operated systems, but allows for repeatable, precise, and dynamic movements. A physician may identify target locations (potentially forming a path) on an image of tissue 22. RCGS 30 relates these digitally selected points to positions within the patient's actual/physical anatomy, and may thereafter command control the movement of catheter 26 to the defined positions where the physician or the RCGS 30 can perform the desired diagnostic of therapeutic function. A more complete description of various elements of an RCGS may be found in the following patent applications that are incorporated herein by reference in their respective entireties: International Patent Application Publication No. WO 2009/120982 published Oct. 1, 2009; U.S. Patent Application Publication No. 2009/0247942 published Oct. 1, 2009; U.S. Patent Application Publication No. 2009/0247944 published Oct. 1, 2009; U.S. Patent Application Publication No. 2009/0247993 published Oct. 1, 2009; U.S. Patent Application Publication No. 2009/0248042 published Oct. 1, 2009; U.S. Patent Application Publication No. 2010/0256558 published Oct. 7, 2010; and U.S. Patent Application Publication No. 2011/0015569 published Jan. 20, 2011. Although particular embodiments of an RCGS 30 are described and illustrated in the aforementioned applications, it should be understood that RCGS 30 may assume a variety of different embodiments. For example, RCGS 30 may comprise any of the systems offered for sale by Hansen Medical, Inc. under the trademarks "Magellan" and "Sensei." RCGS 30 may also comprise a magnetic navigation system such as the system offered for sale by Stereotaxis, Inc. under the trademark "Epoch" in which magnetic fields are used to guide an ablation catheter having a magnetic member that is responsive to the generation of the magnetic fields.

Display system 32 is provided to convey information to a physician to assist in diagnosis and treatment. Display system 32 may comprise one or more conventional computer monitors or other display devices. Display system 32 presents a graphical user interface (GUI) to the physician.

The GUI may include a variety of information including, for example, an image of the geometry of tissue 22, electrophysiology data associated with the tissue 22, graphs illustrating voltage levels over time for various electrodes 52 and images of catheter 26 and other medical devices and related information indicative of the position of catheter 26 and other devices relative to the tissue 22.

ECU 34 provides a means for controlling delivery of ablation energy by ablation catheter 26 to tissue 22 and for controlling the operation of various components of system 20 including catheter 26, ablation generator 28, RCGS 30, and display system 32. ECU 34 may further form part of a system for determining the position and orientation of catheter 26 and similar devices within body 24 such as the system offered for sale under the trademark EnSite™ NavX™ by St. Jude Medical, Inc. and described in U.S. Pat. No. 7,263,397, the entire disclosure of which is incorporated herein by reference or the system such as the MediGuide™ Technology offered for sale by St. Jude Medical, Inc. and generally shown and described in, for example, U.S. Pat. No. 7,386,339, the entire disclosure of which is incorporated herein by reference. ECU 34 may comprise one or more programmable microprocessors or microcontrollers or may comprise one or more ASICs. ECU 34 may include a central processing unit (CPU) and an input/output (I/O) interface through which ECU 34 may receive a plurality of input signals including signals generated by ablation generator 28, electrodes 52 and electronic subassembly 54, 54a on catheter 26, and RCGS 30 and generate a plurality of output signals including those used to control and/or provide data to electrodes 52, subassembly 54, 54a, ablation generator 28, RCGS 30 and display system 32.

Field generator 36 is provided to generate magnetic fields used to determine the position and orientation of the distal end 50 of catheter 26. Generator 36 may be disposed at a fixed location and establishes a multi-dimensional coordinate system. The fields generated by generator 36 induce currents in one or more positions sensors in catheter 26 such as coil assembly 108 on subassemblies 54 or 54a. The current induced in coil assembly 108 is dependent upon the location of the coil 111 within the magnetic fields generated by generator 36 and therefore provides an indication of the location of catheter 26 within the magnetic field and within body 24. In one embodiment, field generator 36 includes a set of three orthogonally arranged coils arranged to create magnetic fields within an area including body 24 and to control the strength, orientation and frequency of the fields. Field generator 36 may comprise part or all of a system made available under the trademark MediGuide™ by St. Jude Medical, Inc., and generally shown and described in, for example, U.S. Pat. No. 7,386,339, the entire disclosure of which is incorporated herein by reference. Alternatively, the generator 36 may comprise part or all of the system sold under the trademark "CARTO" by Biosense Webster, Inc.

Figure 9:
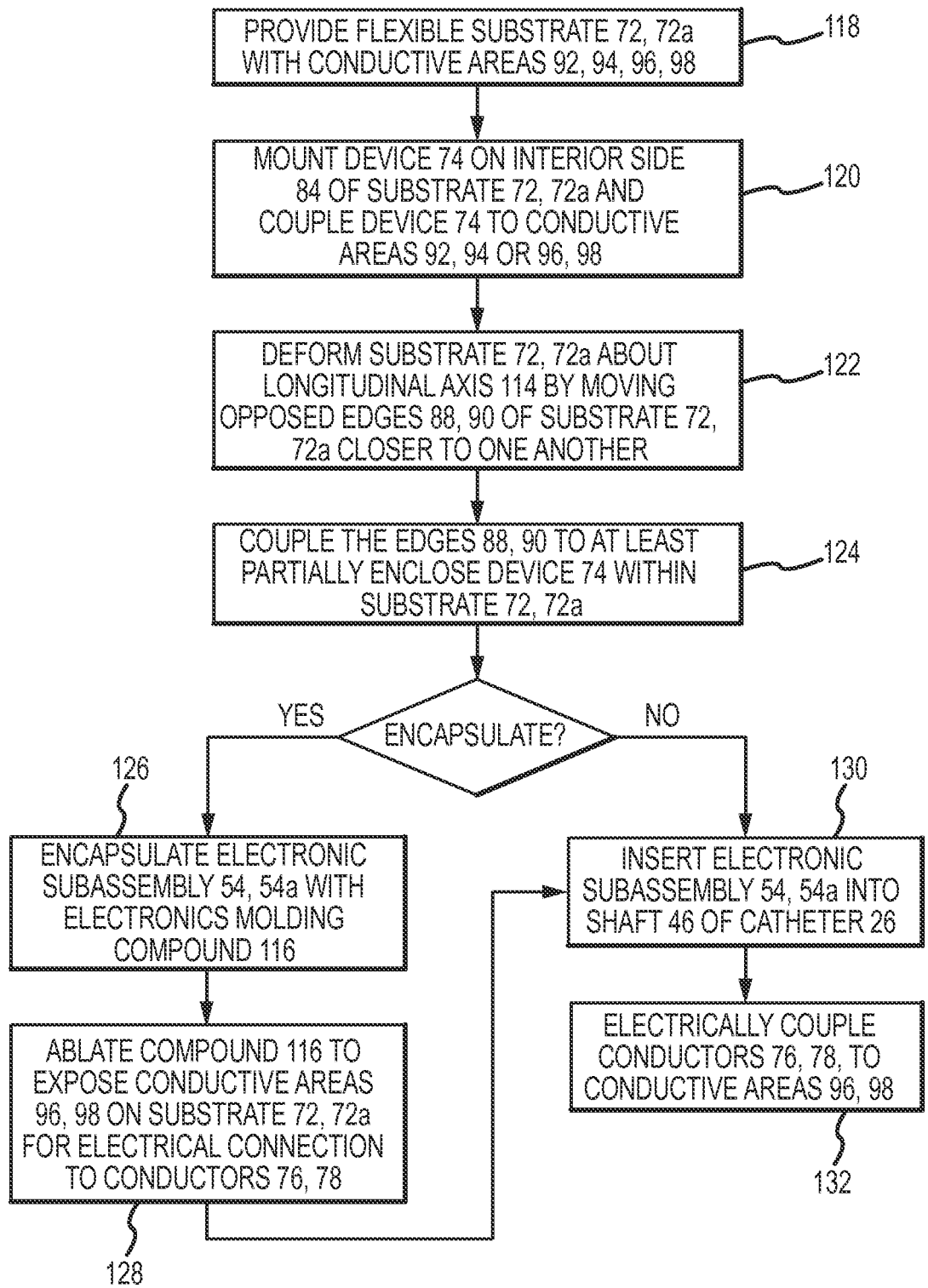
FIG. 9 is a flow chart diagram illustrating various embodiments of a method for fabricating a medical device for diagnosis or treatment of tissue in a body in accordance with the present teachings.

Referring now to FIG. 9, one or more methods for fabricating a medical device 26 for diagnosis or treatment of tissue 22 in body 24 in accordance with the present teachings are illustrated. The method may begin with the process 118 of providing a flexible substrate 72 or 72a. As set forth hereinabove, substrate 72 may include conductive areas 92, 94 on the interior side 84 of substrate 72, conductive areas 96, 98 on the exterior side 86 of substrate 72 and conductive paths 100, 102 extending between the conductive areas 92, 96 and 94, 98, respectively. Substrate 72a may include conductive areas 96, 98 on the exterior side 86 of substrate 72a.

The method may continue with the process 120 of mounting device 74 on the interior side 84 of substrate 72 or 72a and coupling device 74 to one or more conductive areas (such as conductive areas 92, 94 on substrate 72 or conductive areas 96, 98 on substrate 72a). Process 120 may include several subprocesses. In certain embodiments, an adhesive may be applied to one or both of substrate 72, 72a and device 74 to form a bonding area. The adhesive may comprise an ultraviolet (UV) adhesive. It should be understood, however, that other adhesives or epoxies may be used, such as nonconductive epoxies or polyurethane. After the adhesive is applied, the flexible substrate 72, 72a and device 74 may be bonded at the bonding area. Thereafter, the adhesive may be cured. Process 120 may further include electrically connecting device 74 to conductive areas 92, 94 of substrate 72 or conductive area 96, 98 of substrate 72a. Device 74 may be coupled to conductive areas 92, 94 or 96, 98 by soldering leads 110, 112 to conductive areas 92, 94 on substrate 72 or conductive areas 96, 98 on substrate 72a. In such an embodiment, reflowed solder paste may be applied to conductive areas 92, 94 or 96, 98. Types of reflowed solder paste may include type 3 to 6 no-Pb solder pastes, such as Kester 520A SAC305. In accordance with another embodiment, conductive epoxy adhesives, such as Ablebond 2000, may be used to couple leads 110, 112 to conductive areas 92, 94 of substrate 72 or conductive areas 96, 98 of substrate 72a. Solder paste or conductive adhesive may be manually dispensed using a syringe, or it can be dispensed from automated equipment. After the paste or adhesive is applied, device 74 may be positioned such that device 74 contacts the solder paste. Thereafter, substrate 72, 72a and device 74 may then be placed in a curing oven or reflow oven to cure the adhesive and/or reflowed solder paste.

The method may continue with the process 122 of deforming flexible substrate 72, 72a so as to move opposed edges, such as edges 88, 90, closer to one another. In accordance with one embodiment, process 122 may be performed using automated or semi-automated equipment. Substrate 72, 72a is deformed in such a way that it will at least partially enclose device 74. In the illustrated embodiment, for example, substrates 72, 72a may be deformed about axis 114 by bringing edges 88, 90 closer together to deform substrate 72, 72a into a cylindrical shape and circumferentially surround device 74. In other embodiments, substrate 72, 72a may be deformed in a manner that is not axisymmetric and/or not about an axis (longitudinal or otherwise). Substrate 72, 72a can be deformed by folding substrate 72, 72a (at least partially) over device 74. Furthermore, substrate 72, 72a can be deformed and/or folded any number of times to at least partially enclose device 74. Although the illustrated embodiment shows the process 122 of deforming substrate 72, 72a occurring after the process 120 of mounting device 74 to substrate 72, 72a, it should be understood that processes 120, 122 could take place in the opposite order in whole or in part (e.g., device 74 may be mounted to substrate 72, 72a prior to deformation, but leads 110, 112 may be coupled to conductive areas 92, 94 or 96, 98 after deformation).

The method may continue with the process 124 of coupling edges 88, 90 to at least partially enclose device 74 within flexible substrate 72, 72a. Process 124 may include several subprocesses. An adhesive may be applied to one or both of edges 88, 90. The adhesive may comprise a UV cure adhesive so as to provide sufficient adhesive strength in a minimal amount of time. For example, suitable adhesives are Henkel Loctite 3913, 3971, and 3972 cured at 100 mW/cm$^2$ flux. Thereafter, the edges 88, 90 may be overlapped such that the opposed edges 88, 90 are in contact with one another and the adhesive. Finally, the adhesive may be cured. It should be understood that edges 88, 90 may be coupled using other bonding mechanisms, such as mechanical fasteners. Further, edges 88, 90 may be coupled directly to one another or indirectly by coupling overlapping portions of sides 84, 86. Moreover, one of ordinary skill in the art will understand that process 124 is optional and that substrate 72, 72a may at least partially enclose device 74 without coupling edges 88, 90 (directly or indirectly).

In certain embodiments, the method may optionally continue with the process 126 of encapsulating electronic subassembly 54, 54a with electronics molding compound 116. Process 126 may include several subprocesses. Electronic subassembly 54, 54a may be placed in a mold cavity. Thereafter, compound 116 is dispensed into the mold cavity. Compound 116 can be made of Hitachi CEL 9200 (or 9700 series) mold compounds. Suitable silicone LIM materials include Dow-Corning LSR & FLSR series materials. Once compound 116 has cured, electronic subassembly 54, 54a may be removed from the mold cavity. In another embodiment, subassembly 54, 54a may be encapsulated via the "glob top" method. In the "glob top" embodiment, a drop of epoxy or resin may be deposited on the top of subassembly 54, 54a before or after conductors 76, 78 are connected to conductive areas 96, 98. The encapsulant used in the glob top method may be a "chip-on-board (COB) encapsulant", such as (for example and without limitation) those sold under the trademarks Masterbond® and EpoTek® and/or those generally available from Henkel AG & Co. KGaA, Master Bond Inc., Epoxy Technology, Inc., AI Technology, Inc., Shin-Etsu Chemical Co., Ltd., NAMICS Corporation, Zymet Inc., and Hitachi Chemical Co., Ltd. It should be understood that other methods and/or alternative molding materials may be used to encapsulate subassembly 54, 54a, such as (for example and without limitation) silicone liquid injection molding (LIM) and insert injection molding using thermoplastic resins (e.g., polycarbonate).

If electronic subassembly 54, 54a is encapsulated, the method may continue with the process 128 of ablating compound 116 (or the epoxy or resin if encapsulated via the "glob top" method, for example) to expose conductive areas 96, 98 for electrical connection to conductors 76, 78. In accordance with one embodiment, such ablation may be laser ablation with laser energy tuned to ablate organic molding material disposed over conductive areas 76, 78.

Following process 128 (or process 124 if no encapsulation is performed), the method may continue with the process 130 of inserting electronic subassembly 54, 54a into shaft 46 of catheter 26. In one embodiment, tip 62 of shaft 46 may include an orifice into which electronic subassembly 54, 54a may be inserted. Once inserted, the orifice may be filled with an epoxy such as polyurethane to secure electronic subassembly 54, 54a. Alternatively, adhesives may be used. In another embodiment, shaft 46 may include a lumen proximal to tip 62 through which conductors 76, 78 extend and/or irrigation fluid travels. In such an embodiment, electronic subassembly 54, 54a may be attached to structure forming the lumen.

The method may continue with the process 132 of electrically coupling conductors 76, 78 to conductive areas 96, 98. In accordance with one embodiment, conductors 76, 78 may be soldered to conductive areas 96, 98 In such an embodiment, reflowed solder paste may be applied to conductive areas 96, 98. Types of reflowed solder paste may include type 3 to 6 no-Pb solder pastes, such as Kester 520A SAC305. In accordance with another embodiment, conductive epoxy adhesives, such as Ablebond 2000, may be used to couple conductors 76, 78 with conductive areas 96, 98. Solder paste or conductive adhesive may be manually dispensed using a syringe, or it can be dispensed from automated equipment. Once conductors 76, 78 are coupled to conductive areas 96, 98, the solder paste (or conductive adhesive) may be cured in an oven.

A medical device and method for making the same in accordance with the present teachings is advantageous relative to conventional devices and methods. A medical device and method for making the same in accordance with the present teachings provide a more robust and compact sensor and a reliable connection between the sensor and proximally-extending conductors, all while maintaining or improving the functionality of the device. In addition, the method for making the device is less complex and less expensive than conventional methods and results in smaller failure rates during post-fabrication testing.

Although several embodiments of this disclosure have been described above with a certain degree of particularity, those skilled in the art could make numerous alterations to the disclosed embodiments without departing from the scope of this disclosure. All directional references (e.g., upper, lower, upward, downward, left, right, leftward, rightward, top, bottom, above, below, vertical, horizontal, clockwise and counterclockwise) are only used for identification purposes to aid the reader's understanding of the present disclosure, and do not create limitations, particularly as to the position, orientation, or use of the disclosed embodiments. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not as limiting. Changes in detail or structure may be made without departing from the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A medical device for diagnosis or treatment of tissue in a body, comprising:
    an elongate, tubular, deformable shaft comprising a proximal end and a distal end;
    an electronic subassembly disposed within said shaft, said electronic subassembly including
    a flexible substrate comprising an interior side and an exterior side opposite said interior side, said flexible substrate defining a first conductive area; and
    an electronic device mounted on said interior side of said flexible substrate and coupled to said first conductive area, said electronic device at least partially enclosed within said flexible substrate;

a conductor coupled to and extending from said electronic subassembly; and wherein said flexible substrate is cylindrical in shape and circumferentially surrounds said electronic device, and said shaft is deformable along an entire length between the distal end and the proximal end.

2. The device of claim 1, wherein said electronic device is an electromagnetic field detector.

3. The device of claim 2 wherein said electromagnetic field detector comprises a coil defined by a continuous wire element disposed in a helix.

4. The device of claim 3 wherein said electromagnetic field detector further comprises a core, said coil wound about said core.

5. The device of claim 1 wherein said first conductive area is on said interior side of said flexible substrate, said electronic subassembly further includes a second conductive area on said exterior side and a first conductive path between said first and second conductive areas, and said conductor is coupled to said second conductive area.

6. The device of claim 5 wherein said first and second conductive areas are disposed at a proximal end of said flexible substrate.

7. The device of claim 1 wherein said electronic subassembly is encapsulated by an encapsulant.

8. The device of claim 7 wherein first conductive area is on said interior side of said flexible substrate and said electronic subassembly further includes a second conductive area on said exterior side and is exposed through said encapsulant for connection to said conductor.

9. A medical device for diagnosis or treatment of tissue in a body, comprising:

an elongate, tubular, deformable shaft comprising a proximal end and a distal end;

an electronic subassembly disposed within said shaft, said electronic subassembly including a flexible substrate comprising an interior side and an exterior side opposite said interior side, said flexible substrate defining a first conductive area; and an electronic device mounted on said interior side of said flexible substrate and coupled to said first conductive area, said electronic device at least partially enclosed within said flexible substrate;

a conductor coupled to and extending from said electronic subassembly; and wherein said electronic device is an electromagnetic field detector, and said shaft is deformable along an entire length between the distal end and the proximal end.

10. The device of claim 9 wherein said electromagnetic field detector comprises a coil defined by a continuous wire element disposed in a helix.

11. The device of claim 10 wherein said electromagnetic field detector further comprises a core, said coil wound about said core.

12. The device of claim 9 wherein said first conductive area is on said interior side of said flexible substrate, said electronic subassembly further includes a second conductive area on said exterior side and a first conductive path between said first and second conductive areas, and said conductor is coupled to said second conductive area.

13. The device of claim 12 wherein said first and second conductive areas are disposed at a proximal end of said flexible substrate.

14. The device of claim 9 wherein said electronic subassembly is encapsulated by an encapsulant.

15. The device of claim 14 wherein first conductive area is on said interior side of said flexible substrate and said electronic subassembly further includes a second conductive area on said exterior side and is exposed through said encapsulant for connection to said conductor.

16. A method for fabricating a medical device for diagnosis or treatment of tissue in a body, comprising:

providing a flexible substrate comprising an interior side and an exterior side opposite said interior side and first and second edges extending between said interior and exterior sides, said flexible substrate defining a first conductive area;

mounting an electronic device on said interior side of said flexible substrate and coupling said electronic device to said first conductive area;

deforming said flexible substrate so as to at least partially enclose said electronic device;

inserting said flexible substrate into an elongate, tubular, deformable shaft comprising a proximal end and a distal end, the deformable shaft being deformable along an entire length between the distal and proximal ends;

electrically coupling a conductor to said electronic device;

coupling said first and second edges of said flexible substrate to one another to at least partially enclose said electronic device within said flexible substrate; and wherein said coupling said first and second edges includes applying an adhesive to said first edge of said flexible substrate, overlapping said second edge of said flexible substrate with said first edge such that at least a portion of said second edge contacts said adhesive, and curing said adhesive.

17. The method of claim 16 wherein said deforming comprises moving said first and second edges of said flexible substrate closer to one another.

18. The method of claim 16, wherein said electronic device comprises a coil and said mounting comprises electrically connecting said coil of said electronic device to said first conductive area.

19. The method of claim 16, wherein said deforming comprises deforming said flexible substrate about a longitudinal axis of said electronic device.

20. The method of claim 16, wherein said deforming comprises deforming said flexible substrate into a cylindrical shape.

21. The method of claim 16, wherein said first conductive area is disposed on said interior side of said flexible substrate.

22. The method of claim 16, wherein said flexible substrate includes a second conductive area on said exterior side of said flexible substrate and a first conductive path between said first and second conductive areas, said first conductive area disposed on said interior side of said flexible substrate, and electrically coupling said conductor to said electronic device comprises electrically coupling said conductor to said second conductive area.

23. The method of claim 16, further comprising encapsulating said flexible substrate and said electronic device with an encapsulant.

24. The method of claim 23, further comprising ablating said encapsulant to expose said second conductive area on said flexible substrate for connection to said conductor.

25. A method for fabricating a medical device for diagnosis or treatment of tissue in a body, comprising:
- providing a flexible substrate comprising an interior side and an exterior side opposite said interior side and first and second edges extending between said interior and exterior sides, said flexible substrate defining a first conductive area;
- mounting an electronic device on said interior side of said flexible substrate and coupling said electronic device to said first conductive area;
- deforming said flexible substrate so as to at least partially enclose said electronic device;
- inserting said flexible substrate into an elongate, tubular, deformable shaft comprising a proximal end and a distal end, the deformable shaft being deformable along an entire length between the distal and proximal ends;
- electrically coupling a conductor to said electronic device; and
  - wherein said electronic device comprises a coil and said mounting comprises electrically connecting said coil of said electronic device to said first conductive area.

26. The method of claim 25 wherein said deforming comprises deforming said flexible substrate about a longitudinal axis of said electronic device.

27. The method of claim 25 wherein said deforming comprises deforming said flexible substrate into a cylindrical shape.

28. The method of claim 25 wherein said first conductive area is disposed on said interior side of said flexible substrate.

29. The method of claim 25 wherein said flexible substrate includes a second conductive area on said exterior side of said flexible substrate and a first conductive path between said first and second conductive areas, said first conductive area disposed on said interior side of said flexible substrate, and electrically coupling said conductor to said electronic device comprises electrically coupling said conductor to said second conductive area.

30. The method of claim 25 further comprising encapsulating said flexible substrate and said electronic device with an encapsulant.

31. The method of claim 30 further comprising ablating said encapsulant to expose said second conductive area on said flexible substrate for connection to said conductor.

32. The method of claim 25, wherein said deforming comprises moving said first and second edges of said flexible substrate closer to one another.

* * * * *